United States Patent
Chenon et al.

(10) Patent No.: US 7,795,489 B2
(45) Date of Patent: Sep. 14, 2010

(54) METHOD FOR OBTAINING 2,6-DIMETHYLNAPHTHALENE USING ISOMERIZATION AND CRYSTALLIZATION PROCESSES

(75) Inventors: Yang-Ho Chenon, Kyonggi-do (KR); Young-Gyo Choi, Kyonggi-do (KR); Ik-Hyun Kwon, Kyonggi-do (KR)

(73) Assignee: Hyosung Corporation, Kyonggi-do (KR)

( * ) Notice: Subject to any disclaimer, the term of this patent is extended or adjusted under 35 U.S.C. 154(b) by 911 days.

(21) Appl. No.: 11/600,207

(22) Filed: Nov. 16, 2006

(65) Prior Publication Data
US 2007/0299293 A1 Dec. 27, 2007

(30) Foreign Application Priority Data
Jun. 23, 2006 (KR) .................... 10-2006-0057099

(51) Int. Cl.
*C07C 7/14* (2006.01)
(52) U.S. Cl. .................. 585/821; 585/813; 585/814; 585/815; 585/816
(58) Field of Classification Search .......... 585/821, 585/813, 814, 815, 816
See application file for complete search history.

(56) References Cited
U.S. PATENT DOCUMENTS
5,977,426 A * 11/1999 Smith et al. ................ 585/812

| 6,057,487 A | 5/2000 | Munson et al. |
| 6,072,098 A | 6/2000 | Takagawa et al. |
| 2002/0065447 A1 | 5/2002 | Yoshida et al. |
| 2003/0069459 A1 * | 4/2003 | Girotti et al. ............. 585/467 |

FOREIGN PATENT DOCUMENTS

| EP | 0 795 529 A1 | 9/1997 |
| EP | 0 926 114 A2 | 6/1999 |
| EP | 1 151 981 A2 | 11/2001 |
| EP | 1 193 237 A1 | 4/2002 |
| JP | 48-76852 | 10/1973 |
| JP | 49-134634 | 12/1974 |
| JP | 9-249586 | 9/1997 |
| JP | 9-301900 | 11/1997 |
| KR | 2001-0033746 | 4/2001 |
| KR | 10-0469925 | 1/2005 |
| WO | WO 99/33770 A | 7/1999 |

* cited by examiner

Primary Examiner—Tam M Nguyen
(74) Attorney, Agent, or Firm—Nixon & Vanderhye (57) ABSTRACT

High-purity 2,6-dimethylnaphthalene is prepared by (1) subjecting a dimethylnaphthalene isomer mixture rich in 1,5-dimethylnaphthalene, high boiling point materials, unreacted 1,5-dimethyltetralin, and low boiling point materials, which are produced from a dehydrogenation reaction of 1,5-dimethyltetralin, to separation, using a distillation column; subjecting the dimethylnaphthalene mixture separated by the distillation column to liquid state isomerization in the presence of an isomerization catalyst; (3) a first crystallization (melt crystallization process) by cooling the product of liquid state isomerization with a refrigerant without a solvent to form crystals; and (4) a second crystallization (solution crystallization process) of mixing the crystals of the first crystallization step with a solvent to form crystals.

13 Claims, 1 Drawing Sheet

Fig. 1

METHOD FOR OBTAINING 2,6-DIMETHYLNAPHTHALENE USING ISOMERIZATION AND CRYSTALLIZATION PROCESSES

BACKGROUND OF THE INVENTION

1. Field of the Invention

The present invention relates to a method for separation and purification of high-purity 2,6-dimethylnaphthalene, more specifically to a method for separation and purification of 2,6-dimethylnaphthalene (hereinafter referred to as '2,6-DMN'), that separates high-purity 2,6-DMN from 1,5-dimethylnaphthalene (hereinafter referred to as '1,5-DMN') produced from a dehydrogenation reaction of ortho-xylene(o-xylene; OX) and 1,5-butadiene (BD) as raw materials in a combination of isomerization and crystallization processes, thus to obtain high-purity 2,6-DMN in an industrially high yield.

2. Description of the Related Art

The 2,6-naphthalene dicarboxylic acid (hereinafter referred to as '2,6-NDA') is used as a monomer for a polyethylene naphthalate (PEN) resin which is a high-functionality polyester polymer, or as a raw material for polymeric liquid crystals. Particularly, the PEN resin is known to be more excellent in heat resistance, tensile strength, impact strength and barrier property against gases such as oxygen, as compared to widely used polyethylene naphthalate (PEN) resins. Based on such the excellent physical properties, it is expected that the use of the PEN resins will be increased for the purpose of new applications and replacement of the conventional materials, and the demand of 2,6-NDA as a raw materials will be still increased.

There are a variety of the methods for preparation of 2,6-NDA as a raw material for a high-functionality PEN, among the methods, the method for oxidation of 2,6-NDA is a general and economical method. However, in the case of preparation of 2,6-NDA by oxidation of 2,6-DMN, the purity of 2,6-NDA would give great influence on the quality of the product. In particular, in the case where a trace amount of impurities is contained, the impurities would give great influence on the physical properties of the prepared 2,6-NDA, and on the polymerization process of PEN. Thus, for preparation of 2,6-NDA, other isomers (there exist ten isomers of dimethyl naphthalene (DMN) according to the positions two methyl groups) and high-purity 2,6-DMN which is free of impurities. Accordingly, it is required that 2,6-DMN should be also separated and purified at a high purity from a series of mixtures produced from the above-described reactions. Further, in order to easily improve the yield and the purity of separation and purification of 2,6-DMN, conversion to a high content of 2,6-DMN is required during the isomerization process.

Related arts known as the methods for obtaining high-purity and high-content 2,6-DMN can be largely classified into two categories.

One of them is a method for obtaining high-purity and high-content 2,6-DMN method by various separation and purification, and synthesis processes from the naphthalene isomer mixture contained in the liquid state materials which are generated upon the purification of coal or petroleum, and the processing.

The other method is a conventional method, which comprises performing an alkenylation reaction using OX and BD as starting materials in the presence of an alkali catalyst to obtain 5-ortho-tolyl-1-pentene (5-OTP), which is subjected to a cyclization reaction in the presence of a catalyst such as zeolite to obtain 1,5-dimethyltetralin (1,5-DMT), and subsequently, performing a dehydrogenation reaction using 1,5-DMT as a raw material and finally performing an isomerization reaction to obtain 2,6-DMN.

Japanese patent laid-open publication No. S49-134634 and U.S. Pat. No. 3,244,758 describe a method of obtaining o-tolylpentene-2 at a high yield by an alkenylation liquid state reaction using a catalyst such as alkali metals including K, Na or Na/K from OX and BD under the condition of 80 to 175° C., Japanese patent laid-open publication No. S50-8935 describes a method for preparing 1,5-DMT by subjecting o-tolylpentene-2 to cyclization, Japanese patent laid-open publication No. S48-76852 describes a method for preparing 1,5-DMN at a high yield and a high selectivity by subjecting 1,5-DMT to dehydration. Further, Japanese patent laid-open publication No. S50-129534 and U.S. Pat. No. 3,851,002 disclose a method for preparing an isomer mixture mainly consisting of 1,5-, 1,6- or 2,6-DMN by subjecting 1,5-DMN to isomerization, respectively.

Korean Patent No. 10-0469925 discloses a method for preparing 2,6-naphthalenecarboxylic acid ester, which comprises the steps of sequentially isomerizing a DMN mixture mainly consisting of dimethylnaphthalene (DMN) in the presence of a catalyst, crystallizing the isomerization product in the presence of a solvent, separating and recovering the precipitated crystals of 2,6-DMN, distilling the mother liquor after separation of the crystals to remove higher boiling point components and lower boiling point components as compared with DMN and to obtain a DMN residue, while recycling the DMN reside to an isomerization process to prepare a high-purity 2,6-DMN, and a method for preparing 2,6-naphthalenecarboxylic acid ester by liquid state oxidation of the 2,6-DMN obtained from the above-described method to prepare 2,6-NDA, and then esterifying the 2,6-NDA.

Hereinbelow, the conventional isomerization process for obtaining 2,6-DMN from the above-described DMN mixture will be specifically described.

U.S. Pat. No. 4,962,260 discloses a method for converting a DMN isomer mixture consisting of at least one of 1,5-, 1,6-, 1,7- and 1,8-DMNs with a batch or continuous mode liquid state reaction using a zeolite catalyst (which refers to an isomerization catalyst comprising a hydrogenation component of one 8 Group metal, to at least 25% by weight or more of 2,6-DMN isomers, wherein isomerization is performed, using a catalyst which has acid-treated USY zeolite having a $SiO_2/Al_2O_3$ ratio of 4 to 10 and pore windows provided by 12-membered rings containing oxygen and a unit cell size of from about 24.2 to about 24.7 angstroms and at a reaction temperature in the range of from 200 to 400° C., a reaction pressure of 0.3 to 10 atm, and a weight hourly space velocity (WHSV) of 0.2 to 20 $hr^{-1}$, and comprising inorganic materials such as a Group VIII metal, i.e., palladium, platinum or nickel, supported on a support material of alumina, silica-alumina, bentonite, and magnesia.

The invention disclosed in U.S. Pat. No. 4,783,569 is a gas state isomerization process comprising converting at least one 2,6-DMN isomer to a 2,6-triad having an equilibrium composition using a low-acidity, supported, and molecular-sieve-based catalyst, and simultaneously reducing the content of the isomers other than the 2,6-triad, and specifically, a process in which, as a catalyst, a supported crystalline borosilicate molecular sieve of supported crystalline aluminosilicate molecular sieve was used, and isomerization was performed under the condition of a ratio $SiO_2/Al_2O_3=50$ to 150, and a reaction temperature of 250 to 400° C., 200 to 300° C. (in the case of a molecular sieve).

As such, the per se known methods for preparation of 2,6-DMN comprise separation of 2,6-DMN from a DMN isomer mixture by a distillation operation, or by using a catalyst, while the boiling points of the DMN isomers are close each other, and it is thus considerably difficult to perform separation and purification of 2,6-DMN.

Among the DMN isomers, 2,6-DMN has a highest melting point. Thus, 2,6-DMN can be separated and purified by a crystallization process. As such the method for separation of 2,6-DMN, there have been suggested a method by crystallization, a method by adsorption, a method for decomposing a complex by using a certain kind of an organic compound to form a complex with 2,6-DMN, and then separating the complex.

The related art involving crystallization separation and purification of 2,6-DMN will be described below.

Korean patent laid-open publication No. 2001-33746 suggests a method for preparation of 2,6-DMN at a high purity and a high yield, which comprises a series of steps of fraction, crystallization and adsorption from a DMN isomer mixture, without limiting the 2,6-DMN used in the preparation of PEN to certain isomers which are present in the supplied raw materials, the method involving, after performing the crystallization step, as a final purification step, dissolving the isomer mixture in p-, or o-xylene to perform adsorption and separation. Further, Japanese patent laid-open publication No. H9-301900 suggests a method for preparation of 2,6-DMN, which comprises performing crystallization from a DMN isomerization product to precipitate 2,6-DMN, from which a high-purity 2,6-DMN is obtained at a high yield, and a desirable, well-filterable 2,6-DMN crystals are precipitated, to industrially separate and recover a high-purity 2,6-DMN from the DMN isomerization product in the presence of a solvent by a process of a crystallization of 2,6-DMN. Examples of the solvent used for isomerization include pentene, hexane, heptane, octane, nonane, decane, undecane, dodecane, cyclopentane, cyclohexane, methylcyclopentane, methylcyclohexane, cyclooctane, methylcyclooctane, decane, methyldecane, and dimethyldecane. Japanese patent laid-open publication No. H9-249586 discloses a method for separation and recovery of 2,6-DMN, which is industrially favorable, and which comprises performing crystallization from a DMN isomer mixture to precipitate 2,6-DMN, from which a high-purity 2,6-DMN is obtained, and a long-term stability and a desired purity thereof can be maintained.

However, among the suggested, well-known methods, the method by crystallization is approved to be very simple and suitable as an industrial separation method, but it has a complicated process and a relatively low yield, and uses an expensive solvent, thus causing problems that relatively high fixed investment cost and high production cost are required. Upon reviewing the separation processes by crystallization, specific processes are not disclosed, but mostly they simply use a solvent to perform cooling for crystallization. Further, focus has been placed on the isomerization process or the adsorption process using a catalyst, rather than the crystallization process.

SUMMARY OF THE INVENTION

It is an object of the present invention to provide a method for separation and purification of high-purity 2,6-DMN at a high yield using isomerization and crystallization processes.

DESCRIPTION OF THE PREFERRED EMBODIMENTS

According to a preferred embodiment of the present invention, there is provided a method for separation and purification of 2,6-dimethylnaphthalene, which comprises a step of subjecting a dimethylnaphthalene isomer mixture rich in 1,5-dimethylnaphthalene, high boiling point materials, unreacted 1,5-dimethyltetralin, and low boiling point materials, which are produced from a dehydrogenation reaction of 1,5-dimethyltetralin, to separation, using a distillation column;

a step of subjecting the dimethylnaphthalene mixture separated by the distillation column to liquid state isomerization in the presence of an isomerization catalyst;

a first crystallization step (melting crystallization process) of cooling the product of liquid state isomerization with a refrigerant without a solvent to form crystals; and a second crystallization step (solution crystallization process) of mixing the product of the first crystallization step with a solvent to form crystals.

According to another preferred embodiment of the present invention, the purification by a distillation column comprises a step of separation and purification of low boiling point materials to separate low boiling point materials; and a step of separation and purification of high boiling point materials to separate high boiling point materials. The condition for operating the distillation column at the step of separation and purification of low boiling point materials is preferably such that the pressure and the temperature of the top of the tower are 60 to 150 mmHg and 160 to 200° C., respectively, and the temperature of the bottom of the tower is 176 to 220° C. The condition for operating the distillation column at the step of separation and purification of high boiling point materials is preferably such that the pressure and the temperature of the top of the tower are 30 to 80 mmHg and 158 to 170° C., respectively, and the temperature of the bottom of the tower is 190 to 250° C.

According to still another preferred embodiment of the present invention, the liquid state isomerization of the dimethylnaphthalene mixture is performed in a fixed bed continuous reactor, wherein the dimethylnaphthalene mixture may comprise 0.5 to 15.0% by weight of 2,6-dimethylnaphthalene and 60.0 to 97.0% by weight of 1,5-dimethylnaphthalene based on the total amount. Further, the liquid state isomerization of the dimethylnaphthalene mixture is preferably performed at a normal pressure (1 atm) and a reaction temperature in the range of 250 to 320° C. The reaction preferably proceeds at a weight hourly space velocity (WHSV) of 2 to 4 $hr^{-1}$.

According to still another preferred embodiment of the present invention, the liquid state isomerization is performed in the presence of an isomerization catalyst, wherein the isomerization catalyst is a hydrogen-ion-exchanged zeolite beta and may have a molar ratio of $SiO_2/Al_2O_3$ of 5 to 300.

According to still another preferred embodiment of the present invention, the isomerization catalyst is preferably in the pellet form.

According to still another preferred embodiment of the present invention, the first crystallization step is run in a batch or continuous mode, the refrigerant is a mixture of ethylene glycol and water, or technical grade methanol, and the cooling temperature is preferably in the range of 90 to 0° C.

According to still another preferred embodiment of the present invention, the solvent for the second crystallization step is preferably at least one selected from the group consisting of alcohol having 1 to 6 carbon atoms, acetone, hexane and heptane.

According to still another preferred embodiment of the present invention, it is preferable that the solvent for the second crystallization step is further used for crystallization, and then the separated dimethylnaphthalene isomers are directed to the step of injecting the raw materials for recycling.

According to still another preferred embodiment of the present invention, it is preferable that the cooling temperature of the second crystallization step is in the range of 50 to $-20°$ C., and the mixing ratio of the solvent: the dimethylnaphthalene isomer mixture including 2,6-dimethylnaphthalene for the second crystallization step, is 10:1 to 20:1.

According to still another preferred embodiment of the present invention, the cooling rates of the first crystallization step and the second crystallization step are preferably in the range of 0.5 to 1° C./min.

According to still another preferred embodiment of the present invention, the isomer mixture at the first crystallization step preferably comprises 35 to 50% by weight of the dimethylnaphthalene isomer mixture.

According to still another preferred embodiment of the present invention, the dimethylnaphthalene isomer mixture at the second crystallization step preferably comprises 75 to 95% by weight of 2,6-dimethylnaphthalene.

The process for separation and purification of 2,6-DMN according to the present invention comprises:

1) a step of subjecting the dimethylnaphthalene isomer mixture rich in 1,5-DMT, high boiling point materials, unreacted 1,5-DMT, and low boiling point materials, which are produced from a dehydrogenation reaction of 1,5-DMT, to separation by purification using a distillation column;

2) a step of subjecting the high boiling point materials and the DMN isomers to separation after the step 1);

3) a step of subjecting the separated DMN isomer mixture to isomerization for converting it into a mixture rich in 2,6-DMN in the isomerization reactor after the step 2);

4) a first crystallization step of selectively separating the DMN isomer mixture including 2,6-DMN from the DMN isomer mixture rich in 2,6-DMN in a first crystallization by a melting crystallization process;

5) a second crystallization step of separating high-purity 2,6-DMN from the DMN isomer mixture including 2,6-DMN in a second recrystallization by a solution crystallization process;

6) a step of separating the mother liquor separated in the first and second crystallization steps in the distillation columns to a solvent and DMN isomers; and 7) a step of further using the solvent separated in the step 6) for crystallization and recycling the separated DMN isomers to the step 1).

Figure 1:
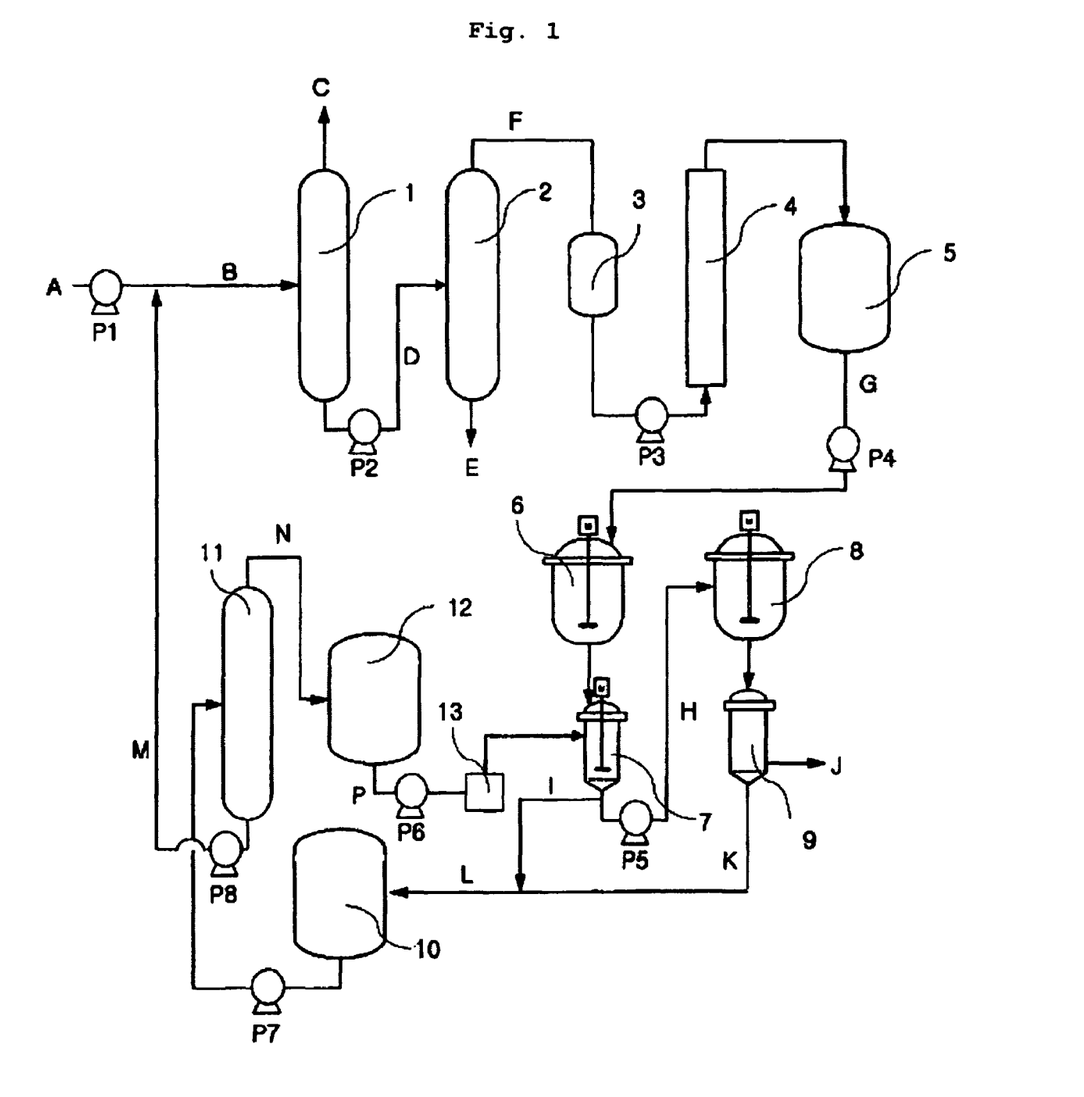
FIG. 1 schematically shows one embodiment of a device for preparation of 2,6-dimethylnaphthalene, coupled with a distillation column, and isomerization and crystallization processes, according to the present invention.

FIG. 1 illustrates one embodiment of the device according to the present invention to carry out the above-described process. The capital letters in FIG. 1 depict the mixture introduced to the units, respectively, and the arrow symbol depicts the moving path of the mixture. With reference to FIG. 1, the process of the present invention is schematically explained.

In order to separate a mixture (A) comprising 95% or more of the 1,5-DMN isomers which are prepared by dehydrogenation of 1,5-dimethyltetralin as a starting raw material, into DMT, 5-OTP, OX, or the like, the mixture (A) is introduced to a distillation column (1) for purification of low boiling point materials by a first pump (P1). In this case, the mixture (A) is mixed with the DMN isomer mixture (M) which is recycled, and then introduced in the form of a mixture (B) to a distillation column (1) for purification of low boiling point materials. Among the mixture introduced to the distillation column (1) for purification of low boiling point materials, the low boiling point materials (C) are separated into the top under certain conditions of pressure and temperature, while the DMN isomer mixture and a mixture (D) of high boiling point materials are flowed into a distillation column (2) for purification of DMN by a second pump (P2) for the next step. Among the mixture (D) introduced to the distillation column (2) for purification of DMN, a DMN isomer mixture (F) is separated into the top under certain conditions of pressure and temperature, while the high boiling point materials (E) are separated into the bottom. The DMN gas which is evaporated by a vacuum suction from the DMN isomer mixture (F) separated from the top of the distillation column (2) for purification is condensed by a condenser, and the condensed DMN isomer mixture is introduced to a first DMN reservoir (3) and then flowed into an isomerization reactor (4) by a third pump (P3). Then, the mixture is transported to a second DMN reservoir (5) rich in 2,6-DMN through isomerization at a normal pressure and a certain range of temperatures. Thereafter, the DMN isomer mixture (G) rich in 2,6-DMN flowed into the DMN reservoir, is introduce to a first crystallizer (6) equipped with a baffle and a draft tube by a fourth pump (P4). Cooling the temperature of the mixture (G), starting from the melting point or higher of the sample to be introduced to the first crystallizer (6) to the crystal generating point using a refrigerant which circulates in the outer jacket of the first crystallizer, and then the mixture was sent to a first vacuum suction filter (7). A first crystal obtained in the first vacuum suction filter (7) by cooling is separated into solid and liquid, and then the first separated mother liquor (I) is supplied to a mother liquor reservoir (10) by vacuum suction filtration. After suction filtration in the first vacuum suction filter (7), the remaining first crystal is dissolved in hot ethanol which is introduced from an ethanol reservoir (12) by a sixth pump (P6) through a heat exchanger (13), and then flowed into a second crystallizer (8) by a fifth pump (P5). The first crystallization solution (H) which is flowed into the second crystallizer (8) and is dissolved at a high temperature is cooled to a crystallization temperature or lower using a refrigerant which circulates in the outer jacket of the second crystallizer as in the first crystallizer, and then the mixture was sent to a second vacuum suction filter (9). A second crystal product (2,6-DMN) (J) and a second separated mother liquor (K) are separated in a second vacuum suction filter (9) equipped with a filter by vacuum suction filtration. The separated high-purity 2,6-DMN crystal (J) is discharged, and the second separated mother liquor (K) is supplied to a mother liquor reservoir (10). Then, the mother liquor (L) supplied to the mother liquor reservoir (10) is introduced to a column for separation of ethanol and the DMN mixture by a seventh pump (P7). Ethanol and the DMN mixture introduced to the distillation column (11) for separation of ethanol and the DMN mixture are separated into ethanol and the DMN mixture, and ethanol (N) separated at the top is collected into an ethanol reservoir (12). Thus separated DMN mixture (M) is further introduced to a distillation column (1) for purification of low boiling point materials, together with a mixture (A) comprising 95% or more of the 1,5-DMN isomers, which are produced from a dehydrogenation reaction of 1,5-dimethylnaphthalene, using an eighth pump (P8).

Each of the above-described processes will be explained in detail.

The dimethylnaphthalene isomer mixture as a raw material introduced to the distillation column (1) for purification of low boiling point materials are a mixture comprising isomers rich in 1,5-DMN, and high boiling point and low boiling point hydrocarbons, which are produced from dehydrogenation of 1,5-DMT. Further, the mixture further comprises 2,6-DMN, 1,6-DMN, 1,5-DMN and other materials, which are recycled to a distillation column after separation and purification for crystallization, in the amounts as depicted in the following Table 1, respectively.

TABLE 1

Composition and physical properties of dimethylnaphthalene isomer mixture (raw material)

| Compound | Composition (% by weight) | Boiling point (° C.) | Melting point (° C.) |
|---|---|---|---|
| 1,5-DMN | 20.0 to 95.0 | 262 | 112 |
| 2,6-DMN | 20.0 to 2.50 | 269 | 82 |
| 1,6-DMN | 25.0 to 1.50 | 266 | −16 |
| Other DMN isomers | to 0.00 | 260 to 270 | — |
| Low boiling point materials[a)] | 17.0 to 0.50 | — | — |
| High boiling point materials[b)] | 17.0 to 0.50 | — | — |
| Total | 100.00 | — | — |

*[a)]Low boiling point materials: (<C12; materials having higher boiling points than those of DMN),
[b)]High boiling point materials: (>C12; materials having lower boiling points than those of DMN)

As shown in Table 1, the present invention allows preparation, separation and purification of high-purity 2,6-DMN, which is economical and industrially useful, from a DMN isomer mixture comprising 1,5-DMN in a certain range of amounts.

According to the present invention, the low boiling point materials and the high boiling point materials, which are contained in the raw materials of 1,5-DMN, are removed in two distillation columns connected in series. Further, the DMN isomer mixture comprising 1,5-DMN and 1,6-DMN as main components, which are separated from the crystallization process, are recycled, combined with raw materials which are a product of a dehydrogenation reaction, and then supplied.

The distillation column is made of stainless steel, and the inner side of the distillation column is filled with packings, such that the distillation column is designed and fabricated to comprise 15 theoretical stages. Separation of the distillation column is designed so as to allow separation according to the injected amount of 5 kg/hour. Specifically, a raw material in an amount of 5 kg/hour is injected, and the total amount of the exiting materials at the top and the bottom of the column is to be 5 kg/hour.

The mixture (B), which is introduced to the distillation column for separation and purification of low boiling point materials as a first distillation column, comprises the unreacted materials among the introduced raw materials, and the compounds, which are by-product, such as naphthalene, 1-methylnaphthalene, 1,5-DMT, 5-OTP and OX. Such the low boiling point materials are separated into the top of the distillation column for removal. The reason why a distillation column for separation and purification of the low boiling point materials is needed is that the components of the low boiling point materials are supplied as unreacted materials and raw materials for by-products, as well as are accumulated by recirculation of 1,5-DMN, and thus it is necessary that they should be removed. Further, the rate of removal of the low boiling point materials may be increased or decreased depending on the components contained in the raw materials and the components contained in the by-products which are produced during isomerization, and thus the energy and the yield of production may be controlled.

The components of the low boiling point materials removed in the distillation column can be crystallized according to the temperature of the condenser at the top of the distillation column. As the temperature controlled at the top of the column is higher, the rate of removal of low boiling point impurities is increased, but the loss of DMN is also correspondingly increased. Accordingly, the control using reflux at the top of column is required, and the rate of recirculation of 1,5-DMN can be regulated according to the temperature and the composition.

The temperature of the condenser at the top of the column can be regulated by controlling the pressure of the evaporated water. The product (D) obtained by removing the low boiling point materials which are the products at the bottom is transported to the second distillation column.

The condition for operation of the distillation column for removing the first low boiling point materials is such that the pressure and the temperature of the top of the column are 60 to 150 mmHg and 160 to 200° C., respectively, and the temperature of the bottom of the column is 176 to 220° C. for heating and distillation. The low boiling point materials are removed at the top of the column, and the product at the bottom of the column product is flowed into a second DMN distillation column.

The second distillation column is a distillation column for separation and purification of the high boiling point materials and the DMN isomer mixture (D), and the constitution and the operation thereof are similar to those of the first distillation column, respectively. The temperature and the pressure to be regulated may vary depending on the difference in the components. The temperature and the pressure to be regulated are as described in Examples. Vapor (DMN isomer) (F) obtained at the top of the column is condensed by a condenser, and the products, excluding a certain amount of portions of the products to be partially recycled, is directed to an isomerization process in the liquid state. The products (E) at the bottom, which are high boiling point materials, are removed.

The condition for operation of the distillation column for removing the second low boiling point materials is such that the temperature and the pressure of the top of the column are 158 to 170° C. and 30 to 80 mmHg, respectively, and the temperature of the bottom of the column is 190 to 250° C. Under such the condition, the DMN isomer (F) is separated into the top of the column, and the high boiling point materials (E) separated into the bottom of the column, which are removed, respectively. Each of the compositions of the components introduced to isomerization is shown in the following Table 2.

TABLE 2

| Compound | Composition (% by weight) |
|---|---|
| 1,5-DMN | 60.00 to 97.00 |
| 2,6-DMN | 15.0 to 0.50 |
| 1,6-DMN | 20.00 to 1.50 |
| Other DMN isomers | 1.00 to 0.00 |
| Low boiling point materials[a)] | 2.0 to 0.50 |
| High boiling point materials[b)] | 2.0 to 0.50 |
| Total | 100.00 |

*[a)]Low boiling point materials: (<C12; materials having higher boiling points than those of DMN),
[b)]High boiling point materials: (>C12; materials having lower boiling points than those of DMN)

The DMN isomerization of the present invention is a reversible reaction for equilibrium composition of 2,6-DMN (45.6 mol %), 1,6-DMN (46.2 mol %) and 1,5-DMN (8.2 mol %). In the industrial production of 2,6-DMN, there is an additional problem that it is difficult to convert DMN isomers other than 2,6-DMN to desired 2,6-DMN isomers. During the process of DMN isomerization, the methyl group is likely to move from an alpha position such as 1, 4, 5 and 8 positions to a beta position such as 2, 3, 6 and 7 positions, or if moving in the opposite direction, the methyl group on the naphthalene ring is likely to move. However, it is known that the methyl group is rearranged from one beta position to another beta position. According to a reference material, the DMN isomers are classified to a group termed as an easily isomerizable triad. The triads are 1) 1,5-DMN, 1,6-DMN and 2,6-DMN; 2) 1,7-DMN, 1,8-DMN and 2,7-DMN; and 3) 1,3-DMN, 1,4-DMN and 2,3-DMN. The tenth isomer, i.e., 1,2-DMN consists of two methyl groups adjacent on alpha and beta positions, and is not consistent with one of the afore-mentioned triads.

The present invention provides a method for preparing 2,6-DMN at a high yield and a high selectivity by subjecting 1,5-DMN and 1,6-DMN to isomerization, using a zeolite catalyst comprising a zeolite beta catalyst having a $SiO_2/Al_2O_3$ ratio of 5.0 to 300, in particular, a zeolite catalyst in the pellet form.

The isomerization process according to the present invention will be explained in detail.

Isomerization of the 1,5-dimethylnaphthalene can be performed at a normal pressure (1 atm) and a temperature in the range of 250 to 320° C., preferably 280 to 300° C.

The present invention is characterized by using a zeolite beta catalyst having a molar ratio of $SiO_2/Al_2O_3$ of 5.0 or more in the preparation of 2,6-DMN by subjecting 1,5-DMN, 1,6-DMN, 2,6-DMN or a mixture thereof to isomerization.

The zeolite beta used in the present invention is a hydrogen-substituted zeolite beta, having a molar ratio of $SiO_2/Al_2O_3$ of 5 to 300, and a $Na_2O$ content of 0.001 to 10% by weight, preferably 0.1 to 5% by weight. In the case of using a zeolite-beta catalyst having a molar ratio of $SiO_2/Al_2O_3$ of less than 5, the activation point is lowered, thus reducing the conversion rate. On the other hand, in the case of using a molar ratio of $SiO_2/Al_2O_3$ of 300 or more, the reaction activity is too high, thus leading to generation of a side-reaction, and then to increase in the amount to high boiling point materials to be produced, and clogging of the pores. As a result, the conversion rate is drastically reduced. Therefore, the use of a zeolite-beta catalyst having a molar ratio of $SiO_2/Al_2O_3$ of 5 to 300 allows the preparation of 2,6-DMN at a high yield, with a high conversion rate to 2,6-DMN.

The zeolite beta catalyst used in the present invention is characterized in that it is in the pellet form. In order to industrially use the catalyst, the catalyst is required to be fixed in a reactor so as to reduce the loss of the catalyst. With this respect, the catalyst should have a suitable size, and correspondingly a structural strength. That is, in the case of the catalyst having a small size, the density in the catalyst layer is increased. Thus, in the case where the fluid passes through the catalyst layer, the loss of the pressure in the catalyst layer is increased. Accordingly, in order to maintain a suitable flow rate, a large pressure no less than a pressure required for the reaction is necessary. Further, in the case of the weak structural strength, the catalyst form is destroyed and the catalyst size is reduced due to the weight of the fixed layer or the pressure of the fluid, thus leading to loss of the catalyst due to bleeding-out of the catalyst. Thus, the catalyst which is industrially used is required to have a suitable size, i.e., 0.1 mm or more.

Examples of the isomerization catalyst which can be used in the present invention include zeolite beta CP811E-75 manufactured by Zeolyst in the pellet form, and HSZ-930 manufactured by Tosoh Corporation.

Hereinbelow, the method for preparing 2,6-DMN by subjecting the DMN isomer mixture to isomerization according to the present invention will be explained in detail. A hydrogen-ion-substituted zeolite beta catalyst, and DMN, i.e., 1,5-DMN, 1,6-DMN or a mixture thereof are placed into a liquid state fixed bed reactor, and nitrogen is purged to remove air in the reactor. Then, isomerization is performed under the condition such that the reaction temperature is 200 to 400° C., preferably 280 to 320° C., the reaction pressure is 0.8 to 1.2 kg/cm²G, and the weight hourly space velocity (WHSV) is usually 2 to 4 hr$^{-1}$. In the case where a reaction temperature is higher than the above-described range, or the WHSV is lower than the above-described range, a side-reaction for converting it to other isomers, rather than isomerization to desired 2,6-DMN, occurs, while in the case where the reaction temperature is lower than the above-described range, the isomerization rate of 1,5-DMN to 2,6-DMN is lowered. At this time, the zeolite beta is used after drying to remove moisture, and in order to remove moisture, 14 kg of zeolite beta is placed into a furnace set at 500° C. and baked for 5 hours.

The crystallization process of the present invention comprises separation and purification of 2,6-dimethylnaphthalene from the dimethylnaphthalene mixture obtained in the isomerization process, using a melting crystallization or solution crystallization process. In this process, the low-energy consumption is low, the device is simple, the operation is easy and simple, and the fixed investment cost and production cost can be reduced.

The method for crystallization, separation and purification of 2,6-DMN according to the present invention is explained with reference to FIG. 1.

The first crystallization step for selectively separating a dimethylnaphthalene isomer mixture comprising 2,6-dimethylnaphthalene from the dimethylnaphthalene isomer mixture obtained in the isomerization step by a melting or solution crystallization is explained.

The dimethylnaphthalene isomer mixture obtained in the isomerization process is a mixture comprising ten DMN isomers, high boiling point hydrocarbons and low boiling point hydrocarbons, with a mixture of 2,6-DMN, 1,6-DMN, 1,5-DMN and other materials, in the amounts as depicted in the following Table 3, respectively.

TABLE 3

Composition and physical properties of dimethylnaphthalene isomer mixture (raw material)

| Compound | Composition (% by weight) | Boiling point (° C.) | Melting point (° C.) |
| --- | --- | --- | --- |
| 2,6-DMN | 20.0 to 95.0 | 262 | 112 |
| 1,5-DMN | 20.0 to 2.50 | 269 | 82 |
| 1,6-DMN | 25.0 to 1.50 | 266 | −16 |
| 2,7-DMN | 0.40 to 0.00 | 262 | 98 |
| 2,3-DMN | 0.10 to 0.00 | 269 | 104 |
| 1,7-DMN | 0.10 to 0.00 | 263 | −14 |
| 1,8-DMN | 0.10 to 0.00 | 270 | 65 |
| 1,2-DMN | 0.10 to 0.00 | 271 | −3.5 |
| 1,4-DMN | 0.10 to 0.00 | 265 | 6 |
| 1,3-DMN | 0.10 to 0.00 | 265 | −4.2 |
| Low boiling point materials | 17.0 to 0.50 | — | — |
| High boiling point materials | 17.0 to 0.50 | — | — |

As shown in Table 3, the present invention allows separation and purification of high-purity 2,6-DMN at a high yield, which is industrially useful, from a DMN isomer mixture comprising 20 to 95% by weight of 2,6-DMN in a batch or continuous mode. Thus, it has an advantage to allow more efficient separation, as compared with the conventional methods for separation of 2,6-DMN at a lower yield.

The crystallization is performed in a batch or continuous mode. The method for crystallization separation and purification can be performed by a melting crystallization or solution crystallization process. In the case of melting crystallization using no solvent, the temperature is regulated at a temperature allowing higher solubility than that in the case of solution crystallization using a solvent.

The first crystallizer (6) used for the crystallization separation and purification is equipped with an outer jacket in which a refrigerant is circulated, and comprises a cooling crystallizer equipped with a draft tube therein, a cooler and a stirrer. As the stirrer, a stirrer in the marine type (self-manufactured) equipped with a stirring speed controller is used to mix the solution in the crystallizer. At this time, the stirring speed is set at zero to 1000 rpm. The temperatures of the solution in the cooling crystallizer and the thermostat are recorded using a digital temperature measurement device (PT 100Ω) connected with a K-type thermocouple, and the temperature of the cooler is regulated within an error range of ±0.05 K using a freezing thermostat controller equipped with a PID regulator. The refrigerant of the cooler is one obtained by mixing ethylene glycol and water at a ratio of 1:3, or a technical grade methanol. The inner temperature of the crystallizer is controlled using a refrigerant which circulates in the outer jacket, the cooling rate of the crystallizer is controlled using a PID program, the final range of the cooling temperature to be controlled is from 90° C. to 0° C. according to the concentration of the DMN isomer mixture, and the produced crystals are separated from the mother liquor using a vacuum filter. The cooling rate is set at a range of 0.1 to 10° C./min. The reason why the cooling temperature is set within the above-described range, the range of the crystals of 2,6-DMN among the raw materials is within the above-described region. At a temperature lower than the above-described temperature range, the components other than 2,6-DMN get to grow into solid crystals. On the other hand, at a high temperature, there occurs a problem that no crystal is produced. If the cooling rate is not within the above-described range, it is difficult to operate the crystallizer, as well as the growth rate of crystals is high. Thus, there also occurs a problem that a lot of impurities are present in the crystals, thus lowering the purity.

The composition of crystals and the residual solution are analyzed using gas chromatography (hereinafter referred to as 'GC') equipped with a FID (Flame Ionization Detector). If the purity of 2,6-DMN is 75 to 95% by weight or more, the mixture is directed to a second crystallization step by extractive crystallization. The melt crystallization process is performed in the same manner as in the solution crystallization process, except that no solvent is used.

The separation and purification process using the above-described melt crystallization is a crystallization process in a batch or continuous mode. If the purity of 2,6-DMN is 75 to 95% by weight or more, the product is directed to a second crystallization step. Crystallization is performed by separating the crystals and the residual solution in the first crystallizer, directing the crystal product to a second crystallization step, and directing the residual solution to a second crystallizer.

Hereinbelow, a second crystallization step for separation of high-purity 2,6-dimethylnaphthalene having a 2,6-DMN purity of 99% by weight or more from the dimethylnaphthalene isomer mixture comprising the above-described 2,6-DMN having a purity of 45% by weight or more obtained from the first separation and purification in the first crystallization step will be explained.

In the process for separation of 2,6-DMN with a purity of 99% by weight or more from the dimethylnaphthalene isomer mixture comprising the above-described 2,6-DMN using a solution crystallization process, the cooling temperature and the cooling rate of the second crystallizer (8) are set at a range of 50 to −20° C., and a range of 0.1 to 10° C./min, respectively, to form 2,6-DMN crystals. At this time, the reason why the cooling temperature is set at the above-described range, is that the temperature in the above-described range is directed to a temperature for generation of crystals of 2,6-DMN, as well as that most crystals are present at a temperature in the above-described range. At a temperature higher than the temperature in the above-described range, there is no generation of crystals, and thus there is no separation. On the other hand, at a temperature lower than the temperature in the above-described range, the crystals are present, together with other impurities. Further, if the cooling rate is not within the above-described range, there occurs that other impurities in the crystals are subject to crystallization to solids like 2,6-DMN. In the solution crystallization, the mixing ratio of the solvent and the dimethylnaphthalene isomer mixture comprising 2,6-DMN is preferably at 1:1 to 100:1. At a mixing ratio lower than the above-described range, it is difficult to obtain high-purity crystals, while at a mixing ratio higher than the above-described range, the amount of the solvent for extraction relative to the amount of the produced crystals is relatively high, and it is difficult to obtain crystals in the region not causing supersaturation. Particularly, it is preferable that as a solvent used in the solution crystallization process, a solvent which is inert to 2,6-DMN, has a low viscosity, and has a boiling point which is not close to that of 2,6-DMN is used, in that the solvent and the crystals are easily separated, and relatively many crystallized products can be obtained. As the solvent, alcohol having 1 to 6 carbon atoms, acetone, hexane or heptane can be used, and preferably ethanol can be used. In Examples according to the present invention, as the solvent used in the solution crystallization, ethanol is used. The reason why ethanol is used, it is advantageous in view of high solubility, and high crystallinity and purification efficiency for crystallization of high-purity 2,6-DMN, as compared with any other solvent.

In the solution crystallization process, a eutectic melting system in which 2,6-DMN and 2,7-DMN co-exist is formed, while in the melt crystallization process, it is difficult to perform separation at a temperature region lower than such the eutectic melting point. Thus, a solvent is used as a third material to modify the behavior of the phase, to obtain a desired crystal of 2,6-DMN. As such, the method for separation and purification of 2,6-DMN according to the present invention allows separation of 2,6-dimethylnaphthalene at a purity of 99% by weight or more, in a combined process of melting and solution crystallization from a DMN isomer mixture comprising a low-purity 2,6-DMN.

In the crystallization separation and purification process in a batch or continuous mode, the following devices may be further added, in order to solve the problem such as crystallization time and adherence of the crystal onto the surface of the crystallizer.

1) In order to minimize the delay of the crystallization time, a heat transfer area should be increased. Thus, in order to increase the heat transfer area, a draft tube and a baffle are provided within a crystallizer.

2) In order to prevent the phenomenon that the crystals clog onto the crystallizer, a device for scraping off the crystals adhered onto the surface of the crystallization reactor is provided on the blade of the stirrer, to avoid the phenomenon of adherence of crystals onto the crystallizer for crystallization.

3) Further, a low-temperature nitrogen is purged into a crystallizer to reduce the phenomenon of adherence of crystals onto the inner surface of the crystallizer and the agglomeration effect that crystals adhere with each other, and to generate a sufficient stirring effect to reduce the entire temperature gradient of the crystallizer, whereby obtaining an effect of growth into a big crystal and prevention of adherence of the crystal onto the inner surface of the wall.

4) As the other method, mention may be made of a method of using buffing in the inner side and the stirrer in order to reduce the phenomenon of adherence of the crystal onto the surface of the crystallizer.

Hereinbelow, Examples will be explained without limiting the scope of the present invention.

EXAMPLES

1. Separation of Low Boiling Point Materials and High Boiling Point Materials Using a Purification Column Example 1

Using the device as depicted in FIG. 1, the process was performed. In order to remove the low boiling point materials and the high boiling point materials, as by-products or unreacted materials, contained in the raw materials to be injected, that is, the raw materials rich in 1,5-DMN, which had been obtained from the dehydrogenation reaction, two processes using distillation columns were performed. The distillation column was made of stainless steel, and the inner side of the distillation column was filled with packings, such that the distillation column was designed and fabricated to comprise 15 theoretical stages. Separation of the distillation column was designed so as to allow separation according to the amount to be injected of 5 kg/hour. A raw material to be injected in an amount of 5 kg/hour was heated and distilled under the condition for operation of the distillation column for removing the first low boiling point materials such that the pressure and the temperature of the top of the column were 60 mmHg and 160° C., respectively, and the temperature of the bottom of the column was 180° C. The low boiling point materials were removed at the top of the column, and the product at the bottom of the column product was flowed into a second DMN distillation column. The second distillation column was a distillation column for separation and purification of the DMN isomer mixture and the high boiling point materials, and was fabricated under the same design condition as for the first distillation column for removing low boiling point materials. The temperature and the pressure of the top of the second distillation column were 160° C. and 30 mmHg, respectively, and the temperature of the bottom of the column was 190° C. Under such the condition, the DMN isomers were separated into the top of the column, and the high boiling point materials were separated into the bottom of the column product. Only separation and purification processes except for a recycling process were performed in Example 1. Each product was taken, and the results of analysis on the product are shown in Table 4.

Example 2

In Example 2, the same procedure as in Example 1 except that the condition for operation of the distillation column is changed such that the pressure and the temperature of the top of the column for removing the first low boiling point materials are 130 mmHg and 180° C., respectively, and the temperature of the bottom of the column is 200° C.; and the temperature and the pressure of the top of the second DMN distillation column are 165° C. and 45 mmHg, and the temperature of the bottom of the column is 210° C., was performed. Results of analysis on the product of Example 2 are shown in Table 4.

Example 3

In Example 3, the same procedure as in Example 1 except that the composition of the raw materials to be supplied is varied depending on the recycling process, was performed. Results of GC analysis on Example 3 were shown in Table 4.

As seen from the results of Examples 1 to 3, using the distillation column designed according to the present invention, low boiling point materials and high boiling point materials can be easily removed, and as a result, it is possible to obtain pure DMN isomers without low boiling point materials and high boiling point materials.

TABLE 4

| | | Example 1 | | | Example 2 | | | Example 3 | | |
|---|---|---|---|---|---|---|---|---|---|---|
| | Items | Raw materials | Composition of L.P. materials after purification on column | Composition of H.P. materials after purification on column | Raw materials | Composition of L.P. materials after purification on column | Composition of H.P. materials after purification on column | Raw materials | Composition of L.P. materials after purification on column | Composition of H.P. materials after purification on column |
| Composition of mixture (% by weight) | 2,6-DMN | 0.74 | 2.45 | 2.05 | 0.15 | 1.67 | 1.51 | 15.18 | 19.64 | 22.5 |
| | 1,6-DMN | 1.53 | 4.42 | 4.45 | 0.57 | 2.3 | 2.68 | 21.14 | 25.3 | 28.9 |
| | 1,5-DMN | 75.57 | 88.26 | 92.38 | 80.32 | 86.01 | 89.78 | 36.3 | 38.24 | 45.37 |
| | Other DMN Isomers | 0.05 | 0.36 | 0.88 | 0.03 | 0.1 | 0.12 | 0.02 | 0.04 | 0.03 |
| | H.P. materials | 2.91 | 4.23 | 0.09 | 3.56 | 5.37 | 1.24 | 14.09 | 16.27 | 2.56 |

TABLE 4-continued

| | | Example 1 | | | Example 2 | | | Example 3 | |
|---|---|---|---|---|---|---|---|---|---|
| Items | Raw materials | Composition of L.P. materials after purification on column | Composition of H.P. materials after purification on column | Raw materials | Composition of L.P. materials after purification on column | Composition of H.P. materials after purification on column | Raw materials | Composition of L.P. materials after purification on column | Composition of H.P. materials after purification on column |
| L.P. materials | 18.34 | 0.28 | 0.15 | 15.37 | 4.55 | 4.67 | 13.27 | 0.51 | 0.64 |
| Ethanol | 0.00 | 0.00 | 0.00 | 0.00 | 0.00 | 0.00 | 0.00 | 0.00 | 0.00 |
| Total | 100.00 | 100.00 | 100.00 | 100.00 | 100.00 | 100.00 | 100.00 | 100.00 | 100.00 |
| Operational condition Temp. (° C.) | — | 160 | 160 | — | 180 | 165 | — | 160 | 160 |
| Top Temp. (° C.) | — | 180 | 190 | — | 200 | 210 | — | 180 | 190 |
| Bottom Pressure (mmHg) | — | 60 | 30 | — | 130 | 45 | — | 60 | 30 |

2. Isomerization Process

Example 4

The modified zeolite beta used in Example 4 was in the pellet form of Zeolyst CP811e-75 having a molar ratio of $SiO_2/Al_2O_3$ of 75. A fixed bed reactor in the tube form, made of stainless steel, and having an inner diameter of 5 inches and a length of 170 cm was filled with 14 kg of a hydrogen ion-substituted zeolite beta catalyst, nitrogen was sufficiently purged at a temperate raising rate of 5° C./min to 400° C. to remove air in the reactor, then hydrogen was purged at a rate of 100 cc/min, the reduction was performed at 500° C. for 1 hour, and then stabilization was performed under the reaction conditions of 200° C. and 1 KgfG and then reaction was performed at a weight hourly space velocity (WHSV) of 2 $h^{-1}$. The product was taken out and analyzed by GC. The compositions of the reactants and the products are each shown in Table 5.

Example 5

Isomerization was performed in the same manner as in Example 4 except that the reaction temperature was changed to 250° C. The compositions of the reactants and the products were each shown in Table 5.

Example 6

Isomerization was performed in the same manner as in Example 4 except that the reaction temperature was changed to 300° C. The compositions of the reactants and the products were each shown in Table 5.

Example 7

Isomerization was performed in the same manner as in Example 4 except that the reaction temperature was changed to 280° C. The compositions of the reactants and the products were each shown in Table 6.

Example 8

Isomerization was performed in the same manner as in Example 7 except that the WHSV was changed to 4. The compositions of the reactants and the products were each shown in Table 6.

Example 9

Isomerization was performed in the same manner as in Example 4 except that the zeolite beta catalyst was changed to Tosoh HSZ-930 having a molar ratio of $SiO_2/Al_2O_3$ of 27. The product was taken out and analyzed by GC. The compositions of the reactants and the products were each shown in Table 7.

Example 10

Isomerization was performed in the same manner as in Example 9 except that the reaction temperature was changed to 250° C. The product was taken out and analyzed by GC. The compositions of the reactants and the products were each shown in Table 7.

Example 11

Isomerization was performed in the same manner as in Example 9 except that the reaction temperature was changed to 300° C. The compositions of the reactants and the products were each shown in Table 7.

Example 12

Isomerization was performed in the same manner as in Example 9 except that the reaction temperature was changed to 280° C. The compositions of the reactants and the products were each shown in Table 8.

Example 13

Isomerization was performed in the same manner as in Example 12 except that the WHSV was changed to 4. The compositions of the reactants and the products were each shown in Table 8.

Example 14

Isomerization was performed in the same manner as in Example 12 except that the molar ratio of $SiO_2/Al_2O_3$ was changed to 9. The compositions of the reactants and the products were each shown in Table 8.

As seen from the results of Examples 4 to 14, when isomerization was performed using zeolite beta having a molar ratio of $SiO_2/Al_2O_3$ of 75, obtained by modification of Zeolyst CP811e-75, and zeolite beta having a molar ratio of $SiO_2/Al_2O_3$ of 27 of Tosoh HSZ-930, the selectivity to 2,6-DMN was high. Further, it could be seen that under the reaction condition at a normal pressure of the WHSV of 2 $hr^{-1}$ and the reaction temperature of 280° C., the selectivity was high.

TABLE 5

| Items | | Example 4 Reactant | Product | Example 5 Reactant | Product | Example 6 Reactant | Product |
|---|---|---|---|---|---|---|---|
| zeolite beta catalyst used | | Zeolyst CP811e-75 | | Zeolyst CP811e-75 | | Zeolyst CP811e-75 | |
| Reaction temperature (° C.) | | 200 | | 250 | | 300 | |
| WHSV ($hr^{-1}$) | | 2 | | 2 | | 2 | |
| Molar ratio of Si/Al | | 75 | | 75 | | 75 | |
| Components (% by weight) | 1,5-DMN | 92.35 | 42.35 | 95.58 | 20.36 | 95.67 | 12.65 |
| | 2,6-DMN | 2.08 | 15.11 | 2.20 | 36.06 | 2.40 | 40.67 |
| | 1,6-DMN | 4.44 | 39.45 | 1.98 | 39.85 | 1.20 | 43.90 |
| | DMN isomers | 0.88 | 0.85 | 0.11 | 0.15 | 0.05 | 0.07 |
| | Low boiling point materials | 0.09 | 1.98 | 0.05 | 2.38 | 0.34 | 1.33 |
| | High boiling point materials | 0.15 | 0.25 | 0.08 | 1.20 | 0.34 | 1.38 |
| | Others | 0.01 | 0.01 | 0.00 | 0.00 | 0.00 | 0.00 |
| Total | | 100.00 | 100.00 | 100.00 | 100.00 | 100.00 | 100.00 |

TABLE 6

| Items | | Example 7 Reactant | Product | Example 8 Reactant | Product |
|---|---|---|---|---|---|
| zeolite beta catalyst used | | Zeolyst CP811e-75 | | Zeolyst CP811e-75 | |
| Reaction temperature (° C.) | | 280 | | 280 | |
| WHSV ($hr^{-1}$) | | 2 | | 4 | |
| Molar ratio of Si/Al | | 75 | | 75 | |
| Components (% by weight) | 1,5-DMN | 92.78 | 8.11 | 94.51 | 13.62 |
| | 2,6-DMN | 2.15 | 47.29 | 2.93 | 42.35 |
| | 1,6-DMN | 4.80 | 41.37 | 2.14 | 40.07 |
| | DMN isomers | 0.05 | 0.06 | 0.13 | 0.11 |

TABLE 6-continued

| Items | Example 7 Reactant | Product | Example 8 Reactant | Product |
|---|---|---|---|---|
| Low boiling point materials | 0.01 | 1.92 | 0.11 | 2.28 |
| High boiling point materials | 0.12 | 1.25 | 0.18 | 1.57 |
| Others | 0.00 | 0.00 | 0.00 | 0.00 |
| Total | 100.00 | 100.00 | 100.00 | 100.00 |

TABLE 7

| Items | | Example 9 Reactant | product | Example 10 Reactant | product | Example 11 Reactant | product |
|---|---|---|---|---|---|---|---|
| zeolite beta catalyst used | | Tosoh HSZ-930 | | Tosoh HSZ-930 | | Tosoh HSZ-930 | |
| Reaction temperature (° C.) | | 200 | | 250 | | 300 | |
| WHSV ($hr^{-1}$) | | 2 | | 2 | | 2 | |
| Molar ratio of Si/Al | | 27 | | 27 | | 27 | |
| Components (% by weight) | 1,5-DMN | 94.31 | 41.33 | 95.56 | 22.36 | 95.47 | 12.34 |
| | 2,6-DMN | 1.08 | 16.11 | 2.09 | 38.06 | 2.27 | 43.67 |
| | 1,6-DMN | 1.04 | 38.45 | 1.58 | 37.85 | 1.15 | 41.94 |
| | DMN isomers | 0.83 | 0.80 | 0.11 | 0.15 | 0.05 | 0.07 |

TABLE 7-continued

|  | Example 9 | | Example 10 | | Example 11 | |
| --- | --- | --- | --- | --- | --- | --- |
| Items | Reactant | product | Reactant | product | Reactant | product |
| Low boiling point materials | 1.09 | 1.98 | 0.05 | 0.38 | 0.52 | 0.97 |
| High boiling point materials | 1.64 | 1.32 | 0.61 | 1.20 | 0.54 | 1.01 |
| Others | 0.01 | 0.01 | 0.00 | 0.00 | 0.00 | 0.00 |
| Total | 100.00 | 100.00 | 100.00 | 100.00 | 100.00 | 100.00 |

TABLE 8

|  |  | Example 12 | | Example 13 | | Example 14 | |
| --- | --- | --- | --- | --- | --- | --- | --- |
| Items | | Reactant | product | Reactant | product | Reactant | product |
| zeolite beta catalyst used | | Tosoh HSZ-930 | | Tosoh HSZ-930 | | Tosoh HSZ-930 | |
| Reaction temperature (° C.) | | 280 | | 280 | | 280 | |
| WHSV (hr$^{-1}$) | | 2 | | 4 | | 2 | |
| Molar ratio of Si/Al | | 27 | | 27 | | 9 | |
| Components (% by weight) | 1,5-DMN | 93.19 | 9.62 | 94.51 | 17.17 | 95.67 | 15.05 |
| | 2,6-DMN | 1.15 | 45.88 | 2.93 | 39.96 | 2.40 | 40.00 |
| | 1,6-DMN | 3.80 | 41.57 | 2.14 | 41.87 | 1.17 | 43.7 |
| | DMN isomers | 0.05 | 0.06 | 0.13 | 0.19 | 0.13 | 0.17 |
| | Low boiling point materials | 1.1 | 1.92 | 0.11 | 0.28 | 0.29 | 0.73 |
| | High boiling point materials | 0.71 | 0.95 | 0.18 | 0.53 | 0.34 | 0.35 |
| | Others | 0.00 | 0.00 | 0.00 | 0.00 | 0.00 | 0.00 |
| Total | | 100.00 | 100.00 | 100.00 | 100.00 | 100.00 | 100.00 |

3. Crystallization Process

Examples 15 to 17

In Examples 15 to 17, separation and purification processes of a crystallization process according to the supply composition of the raw materials as shown in FIG. 1 were performed. 60 kg of the DMN isomer mixture (crude DMN) containing 22.38 to 47.37% by weight of 2,6-DMN was put into a 100-L first crystallizer equipped with a jacket, in which a refrigerant was circulated to maintain the temperature at 90° C. for 30 minutes, lower the temperature to 5 to 45° C. at a rate of 0.7 K/min, and then maintain the final temperature for crystallization for 30 minutes. Thus produced crystals were transported to a first suction filter, the crystals were separated from the residue, and their components were analyzed by GC. The results of analysis were shown in Table 9. Then, the crystal product obtained by separation to the crystals and the residue remained in the 350-L first suction filter, hot ethanol at 70° C. was added thereto for dissolution, and the solution was sent to a second crystallizer. The second crystallization process was the same as in the first crystallization, except that the final cooling temperature was −15° C., and the ratio of the solvent was 20:1. Further, the obtained crystals were analyzed on their components with GC, and the results were shown in Table 9. Performances of separation according to the supply composition by crystallization and of purification were higher as the purity of 2,6-DMN in the supply was higher. In the case where the purity of 2,6-DMN to be supplied was 45.37% by weight, the purity of crystals obtained after the second crystallization step was 99.24% by weight, and the yield was 95.7%.

Examples 18 to 20

Separation and purification in the crystallization process using the cooling rates according to Examples 18 to 20 were performed as the separation and purification processes depicted in FIG. 1. The same procedure was performed as in Examples 15 to 17, except that the cooling rates in the first and second crystallization processes were changed to 0.1 to 3° C./min. The obtained 2,6-DMN crystals were analyzed by GC, and the results were shown in Table 10.

Examples 21 to 23

Separation and purification in the crystallization process using the crystallization temperatures according to Examples 21 to 23 were performed as the separation and purification processes depicted in FIG. 1. The same procedure was performed as in Examples 15 to 17, except that the final temperature for crystallization in the melt crystallization was changed to 0 to 45° C., and the final temperature for crystallization in the second solution crystallization was changed to 0 to −25° C. The obtained 2,6-DMN crystals were analyzed by GC, and the results were shown in Table 11.

Examples 24 to 26

Separation and purification in the crystallization process using the stirring speeds according to Examples 24 to 26 were performed as the separation and purification processes depicted in FIG. 1. The same procedure was performed as in Examples 15 to 17, except that in the first and second crystallization process, the stirring speeds were changed to 100 to 500 rpm. The obtained 2,6-DMN crystals were analyzed by GC, and the results were shown in Table 12.

Examples 27 to 29

Separation and purification in the crystallization process using the ratios of the solvent according to Examples 27 to 29 were performed as the separation and purification processes depicted in FIG. 1. The same procedure was performed as in Examples 15 to 17, except that after the first melt crystallization, the ratio of the solvent was changed to 12:1 to 20:1 in the second solution crystallization. The obtained 2,6-DMN crystals were analyzed by GC, and the results were shown in Table 13.

Examples 30 to 32

Separation and purification in the crystallization process using the solvent to be used according to Examples 30 to 32 were performed as the separation and purification processes depicted in FIG. 1. The same procedure was performed as in Examples 15 to 17, except that after the first melt crystallization, in the second solution crystallization, the solvent to be used was changed to ethanol, methanol or hexane. The obtained 2,6-DMN crystals were analyzed by GC, and the results were shown in Table 14.

As shown from above, the results obtained from the partial processes in the crystallization separation and purification confirm that as the purity of 2,6-DMN in the supply composition was higher, the cooling rate was lower, the crystallization temperature was higher, the stirring speed was lower, and the ratio of the solvent was higher, the purity of the crystals were higher. However, in the separation and purification of crystallization processes, it is advantageous to use the higher purity of 2,6-DMN in the supply composition due to its higher yield, but since as the cooling rate is higher, the operation time is longer. Thus, it is advantageous to suitably set the cooling rate at 0.7° C./min. Higher crystallization temperature is more advantageous to the purity, but the purity is lowered. Thus, it is advantageous to set the crystallization temperature at 25 to 45° C. according to the supply composition in the first melt crystallization process, and to set the crystallization temperature at −15° C. in the second melt crystallization process. As the stirring speed is lower, the size of the crystal is increased, but at a lower stirring speed, there occurs a phenomenon that the crystals adhere to the wall surface of the crystallizer. Thus, such the problem that the crystals adhere to the wall surface of the crystallizer can be solved by adjusting the configuration of the crystallizer and performing surface-treatment while maintaining the stirring speed at a lowest velocity of 100 rpm or less. As the ratio of the solvent is higher, the purity is increased, but it is economically burdensome to lower the yield and use many solvents. Thus, it is advantage to set the ratio of the solvent at 20:1 in the second crystallization process. Examples of the solvent to be used include C1 to C6 alcohol, hexane and heptane, but the investigation on ethanol, ethanol and hexane confirmed that ethanol exhibited remarkable effects on the size, the shape, the purity and the yield of the crystal. Further, the shape of the crystal can be regulated, and high-purity 2,6-DMN having a size of 100 to 700 mm can be obtained in the process as suggested in Examples.

TABLE 9

Effect of change in the composition of raw materials

| | | Example 15 | | | Example 16 | | | Example 17 | | |
| --- | --- | --- | --- | --- | --- | --- | --- | --- | --- | --- |
| Items | | raw material | First purified crystals | Second purified crystals | Raw materials | First purified crystals | Second purified crystals | Raw materials | First purified crystals | Second purified crystals |
| Components (% by weight) | 2,6-DMN | 27.38 | 75.32 | 89.71 | 35.67 | 87.23 | 97.35 | 45.37 | 95.16 | 99.24 |
| | 1,6-DMN | 27.17 | 7.54 | 5.32 | 31.47 | 6.58 | 0.75 | 40.03 | 1.20 | 0.01 |
| | 1,5-DMN | 14.51 | 5.31 | 3.57 | 13.39 | 4.38 | 0.62 | 12.23 | 0.93 | 0.63 |
| | DMN isomers | 0.03 | 0.01 | 0.00 | 0.12 | 0.03 | 0.01 | 0.00 | 0.00 | 0.00 |
| | Low boiling point materials | 16.12 | 6.59 | 0.65 | 12.00 | 0.75 | 0.39 | 1.75 | 1.32 | 0.02 |
| | High boiling Materials | 14.78 | 5.23 | 0.75 | 7.32 | 1.03 | 0.88 | 0.61 | 1.39 | 0.10 |
| | Others | 0.01 | 0.00 | 0.00 | 0.03 | 0.00 | 0.00 | 0.01 | 0.00 | 0.00 |
| | Total | 100.00 | 100.00 | 100.00 | 100.00 | 100.00 | 100.00 | 100.00 | 100.00 | 100.00 |
| Solvent to be used | | — | — | Ethanol | — | — | Ethanol | — | — | Ethanol |
| Ratio of solvent | | — | — | 20:1 | — | — | 20:1 | — | — | 20:1 |
| Crystallization temperature (° C.) | | — | 5 | −15 | — | 25 | −15 | — | 45 | −15 |
| Cooling rate (° C./min) | | — | 0.7 | 0.7 | — | 0.7 | 0.7 | — | 0.7 | 0.7 |

TABLE 9-continued

Effect of change in the composition of raw materials

| Items | Example 15 | | | Example 16 | | | Example 17 | | |
|---|---|---|---|---|---|---|---|---|---|
| | raw material | First purified crystals | Second purified crystals | Raw materials | First purified crystals | Second purified crystals | Raw materials | First purified crystals | Second purified crystals |
| Stirring speed (rpm) | — | 100 | 100 | — | 100 | 100 | — | 100 | 100 |
| Yield (%) | — | 44.1 | 53.2 | — | 67.2 | 85.3 | — | 87.2 | 95.7 |

TABLE 10

Effect of cooling rate

| | Items | Example 18 | | | Example 19 | | | Example 20 | | |
|---|---|---|---|---|---|---|---|---|---|---|
| | | Raw materials | First purified crystals | Second purified crystals | Raw materials | First purified crystals | Second purified crystals | Raw materials | First purified crystals | Second purified crystals |
| Components (% by weight) | 2,6-DMN | 43.20 | 97.24 | 99.84 | 45.08 | 95.07 | 99.13 | 44.98 | 90.82 | 98.54 |
| | 1,6-DMN | 40.29 | 0.75 | 0.01 | 39.72 | 1.76 | 0 | 39.87 | 4.24 | 0.21 |
| | 1,5-DMN | 14.37 | 0.87 | 0.14 | 13.32 | 2.08 | 0.3 | 13.68 | 3.72 | 0.92 |
| | DMN Isomers | 0.02 | 0.00 | 0.00 | 0.03 | 0.00 | 0.00 | 0.07 | 0.00 | 0.00 |
| | Low boiling point Materials | 1.34 | 0.52 | 0.01 | 0.85 | 0.34 | 0.00 | 0.72 | 0.68 | 0.05 |
| | High boiling point materials | 0.77 | 0.62 | 0.00 | 1.00 | 0.75 | 0.57 | 0.68 | 0.54 | 0.28 |
| | Others | 0.01 | 0.00 | 0.00 | 0.00 | 0.00 | 0.00 | 0.00 | 0.00 | 0.00 |
| | Total | 100.00 | 100.00 | 100.00 | 100.00 | 100.00 | 100.00 | 100.00 | 100.00 | 100.00 |
| Solvent to be used | | — | — | Ethanol | — | — | Ethanol | — | — | Ethanol |
| Ratio of solvent (ethanol:DMN) | | — | — | 20:1 | — | — | 20:1 | — | — | 20:1 |
| Crystallization temperature (° C.) | | — | 45 | −15 | — | 45 | −15 | — | 45 | −15 |
| Cooling rate (° C./min) | | — | 0.1 | 0.1 | — | 0.7 | 0.7 | — | 3 | 3 |
| Stirring speed (rpm) | | 100 | 100 | 100 | 100 | 100 | 100 | 100 | 100 | 100 |
| Yield (%) | | — | 88.1 | 96.5 | — | 87.0 | 94.6 | — | 85.3 | 92.9 |

TABLE 11

Effect of crystallization temperature

| | Items | Example 21 | | | Example 22 | | | Example 23 | | |
|---|---|---|---|---|---|---|---|---|---|---|
| | | Raw materials | First purified crystals | Second purified crystals | Raw materials | First purified crystals | Second purified crystals | Raw materials | First purified crystals | Second purified crystals |
| Components (% by weight) | 2,6-DMN | 43.27 | 98.12 | 99.9 | 44.63 | 96.32 | 99.54 | 45.29 | 94.88 | 99.09 |
| | 1,6-DMN | 42.37 | 0.83 | 0.00 | 43.57 | 0.88 | 0.00 | 41.25 | 2.38 | 0.00 |
| | 1,5-DMN | 10.35 | 0.59 | 0.00 | 10.77 | 2.34 | 0.25 | 10.32 | 1.94 | 0.34 |
| | DMN isomers | 0.03 | 0.00 | 0.00 | 0.02 | 0.00 | 0.00 | 0.05 | 0.00 | 0.00 |
| | Low boiling point materials | 0.95 | 0.15 | 0.00 | 0.5 | 0.25 | 0.00 | 1.34 | 0.37 | 0.00 |
| | High boiling point materials | 3.03 | 0.31 | 0.10 | 0.5 | 0.21 | 0.21 | 1.72 | 0.43 | 0.57 |

TABLE 11-continued

Effect of crystallization temperature

| | | Example 21 | | | Example 22 | | | Example 23 | |
|---|---|---|---|---|---|---|---|---|---|
| Items | Raw materials | First purified crystals | Second purified crystals | Raw materials | First purified crystals | Second purified crystals | Raw materials | First purified crystals | Second purified crystals |
| Others | 0.00 | 0.00 | 0.00 | 0.01 | 0.00 | 0.00 | 0.03 | 0.00 | 0.00 |
| Total | 100.00 | 100.00 | 100.00 | 100.00 | 100.00 | 100.00 | 100.00 | 100.00 | 100.00 |
| Solvent to be used | — | — | Ethanol | — | — | Ethanol | — | — | Ethanol |
| Ratio of solvent (ethanol:DMN) | — | — | 20:1 | — | — | 20:1 | — | — | 20:1 |
| Crystallization temperature (° C.) | — | 45 | 0 | — | 25 | −15 | — | 5 | −15 |
| Cooling rate (° C./min) | — | 0.7 | 0.7 | — | 0.7 | 0.7 | — | 0.7 | 0.7 |
| Stirring speed (rpm) | — | 100 | 100 | — | 100 | 100 | — | 100 | 100 |
| Yield (%) | — | 85.0 | 72.7 | — | 90.6 | 82.4 | — | 97.5 | 94.3 |

TABLE 12

Effect of stirring speed

| | | Example 24 | | | Example 25 | | | Example 26 | | |
|---|---|---|---|---|---|---|---|---|---|---|
| | Items | Raw materials | First purified crystals | Second purified crystals | Raw materials | First purified crystals | Second purified crystals | Raw materials | First purified crystals | Second purified crystals |
| Components (% by weight) | 1,5-DMN | 45.13 | 95.28 | 99.24 | 45.27 | 95.01 | 98.99 | 45.81 | 93.27 | 97.14 |
| | 2,6-DMN | 46.28 | 2.67 | 0.05 | 45.24 | 3.24 | 0.2 | 44.44 | 4.25 | 0.97 |
| | 1,6-DMN | 7.86 | 1.82 | 0.68 | 8.77 | 1.49 | 0.73 | 9.00 | 2.01 | 1.54 |
| | DMN isomers | 0.00 | 0.00 | 0.00 | 0.00 | 0.00 | 0.00 | 0.00 | 0.00 | 0.00 |
| | Low boiling point materials | 0.01 | 0.00 | 0.00 | 0.27 | 0.02 | 0.00 | 0.14 | 0.02 | 0.00 |
| | High boiling point materials | 0.71 | 0.23 | 0.03 | 0.45 | 0.24 | 0.08 | 0.6 | 0.45 | 0.35 |
| | Others | 0.01 | 0.00 | 0.00 | 0.00 | 0.00 | 0.00 | 0.01 | 0.00 | 0.00 |
| | Total | 100.00 | 100.00 | 100.00 | 100.00 | 100.00 | 100.00 | 100.00 | 100.00 | 100.00 |
| | Solvent to be used | — | — | Ethanol | — | — | Ethanol | — | — | Ethanol |
| | Ratio of solvent (ethanol:DMN) | — | — | 20:1 | — | — | 20:1 | — | — | 20:1 |
| | Crystallization temperature (° C.) | — | 45 | −15 | — | 45 | −15 | — | 45 | −15 |
| | Cooling rate (° C./min) | — | 0.7 | 0.7 | — | 0.7 | 0.7 | — | 0.7 | 0.7 |
| | Stirring speed (rpm) | — | 100 | 100 | — | 200 | 200 | — | 500 | 500 |
| | Yield (%) | — | 86.8 | 94.8 | — | 87.0 | 94.6 | — | 86.7 | 93.9 |

TABLE 13

Effect of ratio of solvent

| | | Example 27 | | | Example 28 | | | Example 29 | | |
|---|---|---|---|---|---|---|---|---|---|---|
| | Items | Raw materials | First purified crystals | Second purified crystals | Raw materials | First purified crystals | Second purified crystals | Raw materials | First purified crystals | Second purified crystals |
| Components (% by weight) | 2,6-DMN | 44.65 | 94.19 | 97.21 | 45.05 | 94.32 | 98.14 | 45.74 | 94.13 | 99.91 |
| | 1,6-DMN | 46.32 | 3.71 | 1.71 | 45.37 | 2.80 | 0.31 | 44.97 | 3.45 | 0.00 |
| | 1,5-DMN | 8.27 | 1.52 | 0.88 | 8.27 | 2.64 | 1.35 | 7.34 | 1.42 | 0.05 |
| | DMN isomers | 0.05 | 0.00 | 0.00 | 0.04 | 0.00 | 0.00 | 0.07 | 0.00 | 0.00 |

TABLE 13-continued

Effect of ratio of solvent

| Items | | Example 27 | | | Example 28 | | | Example 29 | | |
|---|---|---|---|---|---|---|---|---|---|---|
| | | Raw materials | First purified crystals | Second purified crystals | Raw materials | First purified crystals | Second purified crystals | Raw materials | First purified crystals | Second purified crystals |
| | Low boiling point materials | 0.07 | 0.00 | 0.00 | 0.07 | 0.00 | 0.00 | 0.38 | 0.00 | 0.00 |
| | High boiling point materials | 0.64 | 0.58 | 0.20 | 1.19 | 0.24 | 0.20 | 1.48 | 1.00 | 0.04 |
| | Others | 0.00 | 0.00 | 0.00 | 0.01 | 0.00 | 0.00 | 0.02 | 0.00 | 0.00 |
| | Total | 100.00 | 100.00 | 100.00 | 100.00 | 100.00 | 100.00 | 100.00 | 100.00 | 100.00 |
| Solvent to be used | | — | — | Ethanol | — | — | Ethanol | — | — | Ethanol |
| Ratio of solvent (ethanol:DMN) | | — | — | 12:1 | — | — | 15:1 | — | — | 20:1 |
| Crystallization temperature (° C.) | | — | 45 | −15 | — | 45 | −15 | — | 45 | −15 |
| Cooling rate (° C./min) | | — | 0.7 | 0.7 | — | 0.7 | 0.7 | — | 0.7 | 0.7 |
| Stirring speed(rpm) | | — | 100 | 100 | — | 100 | 100 | — | 100 | 100 |
| Yield (%) | | — | 87.6 | 96.3 | — | 86.5 | 94.6 | — | 83.6 | 95.2 |

TABLE 14

Effect of solvent to be used

| Items | | Example 30 | | | Example 31 | | | Example 32 | | |
|---|---|---|---|---|---|---|---|---|---|---|
| | | Raw materials | First purified crystals | Second purified crystals | Raw materials | First purified crystals | Second purified crystals | Raw materials | First purified crystals | Second purified crystals |
| Components (% by weight) | 2,6-DMN | 43.22 | 94.60 | 99.75 | 45.19 | 94.32 | 98.00 | 42.98 | 94.54 | 97.12 |
| | 1,6-DMN | 44.05 | 2.70 | 0.02 | 44.64 | 2.52 | 1.09 | 45.87 | 2.10 | 0.37 |
| | 1,5-DMN | 10.37 | 2.26 | 0.15 | 9.37 | 2.69 | 0.6 | 8.21 | 2.15 | 1.97 |
| | DMN isomers | 0.34 | 0.02 | 0.00 | 0.52 | 0.32 | 0.24 | 0.17 | 0.02 | 0.00 |
| | Low boiling point materials | 0.15 | 0.04 | 0.00 | 0.04 | 0.00 | 0.00 | 1.02 | 0.12 | 0.00 |
| | High boiling point materials | 1.86 | 0.38 | 0.08 | 0.22 | 0.15 | 0.07 | 1.74 | 1.07 | 0.54 |
| | Others | 0.01 | 0.00 | 0.00 | 0.02 | 0.00 | 0.00 | 0.01 | 0.00 | 0.00 |
| | Total | 100.00 | 100.00 | 100.00 | 100.00 | 100.00 | 100.00 | 100.00 | 100.00 | 100.00 |
| Solvent to be used | | — | — | Ethanol | — | — | Methanol | — | — | Hexane |
| Ratio of solvent (ethanol:DMN) | | — | — | 20:1 | — | — | 20:1 | — | — | 20:1 |
| Crystallization temperature (° C.) | | — | 45 | −15 | — | 45 | −15 | — | 45 | −15 |
| Cooling rate (° C./min) | | — | 0.7 | 0.7 | — | 0.7 | 0.7 | — | 0.7 | 0.7 |
| Stirring speed (rpm) | | — | 100 | 100 | — | 100 | 100 | — | 100 | 100 |
| Yield (%) | | — | 97.1 | 95.3 | — | 92.5 | 90.4 | — | 85.9 | 83.4 |

4. Continuous Process

Example 33

With reference to FIG. 1, in the optimization of the entire process, including the recycling step, which was continuously run, the operational condition, the process purity, the yield, and the samples produced from each of the processes were analyzed, and the results of GC analysis were shown in Table 15.

Moreover, according to the present invention, for separation and purification, the purification on a distillation column, and the crystallization separation and purification processes can be suitably combined to subject the high boiling point materials and the low boiling point materials, which are produced from the reaction process, to separation and purification. The method for separation and purification of 2,6-DMN by a crystallization process according to the present invention uses about ⅕ of heat of vaporization to be used in the distillation operation, and the energy to be required is saved, and

TABLE 15

| Items | | Raw materials | Composition of L.P. materials after purification on column | Composition of H.P. materials after purification on column | Product of isomerization | First crystallization purified crystal | Second crystallization purified | Recycling composition of mother liquor | Composition of ethanol |
|---|---|---|---|---|---|---|---|---|---|
| Composition of mixture (% by weight) | 2,6-DMN | 0.74 | 12.45 | 12.05 | 45.24 | 95.62 | 99.67 | 5.76 | 0.01 |
| | 1,6-DMN | 1.53 | 19.42 | 19.11 | 38.94 | 1.64 | 0.25 | 54.54 | 0.00 |
| | 1,5-DMN | 75.57 | 63.26 | 67.27 | 5.60 | 2.62 | 0 | 33.27 | 0.00 |
| | Other DMN isomers | 0.05 | 0.36 | 0.88 | 0.37 | 0 | 0 | 0.84 | 0.00 |
| | High boiling point materials | 2.91 | 4.13 | 0.19 | 3.94 | 0.12 | 0.08 | 0.25 | 0.00 |
| | Low boiling point materials | 18.34 | 0.38 | 0.50 | 5.91 | 0 | 0 | 5.24 | 0.00 |
| | Ethanol | 0 | 0 | 0 | 0 | 0 | 0 | 0.1 | 99.99 |
| Total | | 100.00 | 100.00 | 100.00 | 100.00 | 100.00 | 100.00 | 100.00 | 100.00 |
| reaction temperature(° C.) | | — | — | — | 280 | — | — | — | — |
| WHSV(hr$^{-1}$) | | — | — | — | 2 | — | — | — | — |
| Crystallization temperature (° C.) | | — | — | — | — | 90→45 | 50→−15 | — | — |
| Cooling rate (° C./min) | | — | — | — | — | 0.7 | 0.7 | — | — |
| Stirring speed (rpm) | | — | — | — | — | 100 | 100 | — | — |
| Yield (%) | | — | 98.5 | 99.3 | — | 87.5 | 95.5 | — | — |
| Condition of top of distillation column | | — | 60 mmHg 160° C. | 30 mmHg 160° C. | — | — | — | — | — |
| Condition of bottom of distillation column | | — | 180° C. | 220° C. | — | — | — | — | — |

EFFECTS OF THE INVENTION

According to the present invention, there is provided an industrially ready-to-use method for preparing 2,6-dimethylnaphthalene at a high selectivity and a high yield by isomerization of the above-described 1,5-dimethylnaphthalene using a zeolite-beta catalyst. Further, by using a zeolite beta catalyst, in particular, having a molar ratio of $SiO_2/Al_2O_3$ of 5.0 to 300.0 instead of a conventional zeolite Y catalyst, the generation of by-products is reduced, thus obtaining an effect of providing 2,6-DMN at a high selectivity and a high yield. In the step of the isomerization reaction of 1,5-dimethylnaphthalene, the reaction is performed at a normal pressure (1 atm); and a temperature in the range of 250 to 320° C., preferably 280 to 300° C., whereby efficient separation and purification of 2,6-dimethylnaphthalene is made possible.

high-purity 2,6-DMN can be separated at a high yield by a simple solid-liquid separation operation. According to the present invention, the device for separation and purification is simple, and the operation is easy and simple, and the fixed investment cost and the production cost can be reduced. Thus, advantageously, it has economical usefulness.

What is claimed is:

1. A method for separation and purification of 2,6-dimethylnaphthalene, which comprises a step of subjecting a dimethylnaphthalene isomer mixture rich in 1,5-dimethylnaphthalene, high boiling point materials, unreacted 1,5-dimethyltetralin, and low boiling point materials, which are produced from a dehydrogenation reaction of 1,5-dimethyltetralin, to separation, using a distillation column;

a step of subjecting the dimethylnaphthalene mixture separated by the distillation column to liquid state isomerization in the presence of an isomerization catalyst;

a first crystallization step (melt crystallization process) of cooling the product of the liquid state isomerization with a refrigerant without a solvent to form crystals;

a second crystallization step (solution crystallization process) of mixing the crystals produced in the first crystallization step with an ethanol solvent to form crystals a step of separating mother liquor separated in the first and second crystallization steps to a solvent and DMN isomers by distillation; and a step of using the solvent separated in the step of separating the mother liquor for the second crystallization step and recycling the separated DMN isomers in the step of separating the mother liquor to the distillation column, wherein a cooling temperature of the first crystallization step is in the range of 90 to 0° C. and cooling rates of the first crystallization step and the second crystallization step are in the range of 0.5 to 1° C./min, wherein the purification by the distillation column comprises a step of separation and purification of low boiling point materials to separate low boiling materials; and a step of separation and purification of high boiling point materials to separate high boiling materials, wherein the distillation column at the step of separation and purification of low boiling point materials is operated such that the pressure and the temperature of the top of the tower are 60 to 150 mmHg and 160 to 200° C., respectively, and the temperature of the bottom of the tower is 176 to 220° C., and wherein the distillation column at the step of separation and purification of high boiling point materials is operated such that the pressure and the temperature of the top of the tower arc 30 to 80 mmHg and 150 to 170° C., respectively, and the temperature of the bottom of the tower is 190 to 250° C.

2. The method for separation and purification of 2,6-dimethylnaphthalene according to claim 1, wherein the liquid state isomerization of the dimethylnaphthalene mixture is performed in a fixed bed continuous reactor.

3. The method for separation and purification of 2,6-dimethylnaphthalene according to claim 1, wherein the dimethylnaphthalene mixture comprises 0.5 to 15.0% by weight of 2,6-dimethylnaphthalene and 60.0 to 97.0% by weight of 1,5-dimethylnaphthalene based on the total amount.

4. The method for separation and purification of 2,6-dimethylnaphthalene according to claim 1, wherein the liquid state isomerization of the dimethylnaphthalene mixture is performed at a normal pressure (1 atm) and a reaction temperature in the range of 250 to 320° C.

5. The method for separation and purification of 2,6-dimethylnaphthalene according to claim 1, wherein the reaction proceeds at a weight hourly space velocity (WHSV) of 2 to 4 $hr^{-1}$.

6. The method for separation and purification of 2,6-dimethylnaphthalene according to claim 1, wherein the liquid state isomerization is performed in the presence of an isomerization catalyst, and the isomerization catalyst is a hydrogen-ion-exchanged zeolite beta and has a molar ratio of silica/alumina of 5 to 300.

7. The method for separation and purification of 2,6-dimethylnaphthalene according to claim 6, wherein the isomerization catalyst is in the pellet form.

8. The method for separation and purification of 2,6-dimethylnaphthalene according to claim 1, wherein the first crystallization step is run in a batch or continuous mode.

9. The method for separation and purification of 2,6-dimethylnaphthalene according to claim 1, wherein the refrigerant in the first crystallization step is a mixture of ethylene glycol and water, or technical grade methanol.

10. The method for separation and purification of 2,6-dimethylnaphthalene according to claim 1, wherein the cooling temperature of the second crystallization step is in the range of 50 to −20° C.

11. The method for separation and purification of 2,6-dimethylnaphthalene according to claim 1, wherein the mixing ratio of the solvent: the dimethylnaphthalene isomer mixture including 2,6-dimethylnaphthalene for the second crystallization step is 10:1 to 20:1.

12. The method for separation and purification of 2,6-dimethylnaphthalene according to claim 1, wherein the isomer mixture at the first crystallization step comprises 35 to 50% by weight of the dimethylnaphthalene isomer mixture.

13. The method for separation and purification of 2,6-dimethylnaphthalene according to claim 1, wherein the dimethylnaphthalene isomer mixture at the second crystallization step comprises 75 to 95% by weight of 2,6-dimethylnaphthalene.

* * * * *